(12) United States Patent
Knox et al.

(10) Patent No.: US 9,669,238 B2
(45) Date of Patent: Jun. 6, 2017

(54) RADIOTHERAPEUTIC APPARATUS

(71) Applicants: Elekta AB (publ), Stockholm (SE);
Koninklijke Philips Electronics N.V.,
BA Eindhoven (NL)

(72) Inventors: Christopher Knox, East Grinstead
(GB); Duncan Bourne, Redhill (GB);
Johan Overweg, AE Eindhoven (NL);
Jan Rietema, AA Nuenen (NL)

(73) Assignees: Elekta AB (publ), Stockholm (SE);
Koninklijke Philips Electronics N.V.,
Eindhoven (NL)

( * ) Notice: Subject to any disclaimer, the term of this patent is extended or adjusted under 35 U.S.C. 154(b) by 325 days.

(21) Appl. No.: 13/647,595

(22) Filed: Oct. 9, 2012

(65) Prior Publication Data

US 2013/0035586 A1 Feb. 7, 2013

Related U.S. Application Data

(63) Continuation of application No. PCT/EP2011/006100, filed on Dec. 6, 2011.

(30) Foreign Application Priority Data

Dec. 8, 2010 (GB) .................................. 1020805.6
Mar. 30, 2011 (GB) .................................. 1105368.3

(51) Int. Cl.
*A61B 5/05* (2006.01)
*A61N 5/10* (2006.01)
(Continued)

(52) U.S. Cl.
CPC ............ *A61N 5/1049* (2013.01); *A61B 5/055* (2013.01); *A61B 5/4836* (2013.01); *A61N 5/1081* (2013.01); *A61N 2005/1055* (2013.01)

(58) Field of Classification Search
None
See application file for complete search history.

(56) References Cited

U.S. PATENT DOCUMENTS

| 4,402,085 A | 8/1983 | Distler et al. .................. 378/15 |
| 2002/0025023 A1* | 2/2002 | Herold et al. ................ 378/146 |

(Continued)

FOREIGN PATENT DOCUMENTS

| EP | 2359906 | 8/2011 | ............... A61N 5/10 |
| WO | WO 03/008986 A2 | 1/2003 | ............. G01R 33/00 |

(Continued)

OTHER PUBLICATIONS

European Patent Office, International Search Report and Written Opinion, PCT/EP2011/006100, date of mailing May 10, 2012, 3 pages.

(Continued)

*Primary Examiner* — Amanda Lauritzen Moher
*Assistant Examiner* — Shahdeep Mohammed
(74) *Attorney, Agent, or Firm* — Sunstein Kann Murphy & Timbers LLP

(57) ABSTRACT

We provide a radiotherapeutic apparatus comprising a patient support, magnetic coils disposed around the patient support for creating a magnetic field therewithin, a radiation source producing a beam of radiation directed toward the patient support and mounted on a rotatable support thereby to rotate the radiation source around the patient support, a slip ring for conveying electrical power to the radiation source and located around the patient support, including at least one electrical interruption therein. This creates a slip ring in which there is no continuous circumferential path, and one in which the current is therefore forced to take a route via one side or the other.

15 Claims, 7 Drawing Sheets

(51) Int. Cl.
*A61B 5/00* (2006.01)
*A61B 5/055* (2006.01)

(56) References Cited

U.S. PATENT DOCUMENTS

| | | | |
|---|---|---|---|
| 2004/0013239 A1* | 1/2004 | Gregerson | ............... A61B 6/02 378/197 |
| 2007/0167032 A1* | 7/2007 | Angerpointner et al. | ...... 439/22 |
| 2007/0217574 A1 | 9/2007 | Beyerlein | ..................... 378/107 |

FOREIGN PATENT DOCUMENTS

| | | | | |
|---|---|---|---|---|
| WO | WO 2004/024235 A1 | 3/2004 | ............... | A61N 5/10 |
| WO | WO 2005/081842 | 9/2005 | | |
| WO | WO 2006/097274 A1 | 9/2006 | ............. | G01R 33/48 |
| WO | WO 2009/156896 | 12/2009 | ............. | A61B 5/055 |

OTHER PUBLICATIONS

UK Intellectual Property Office, Search Report, GB1020805.6, Feb. 15, 2011, 4 pages.

* cited by examiner

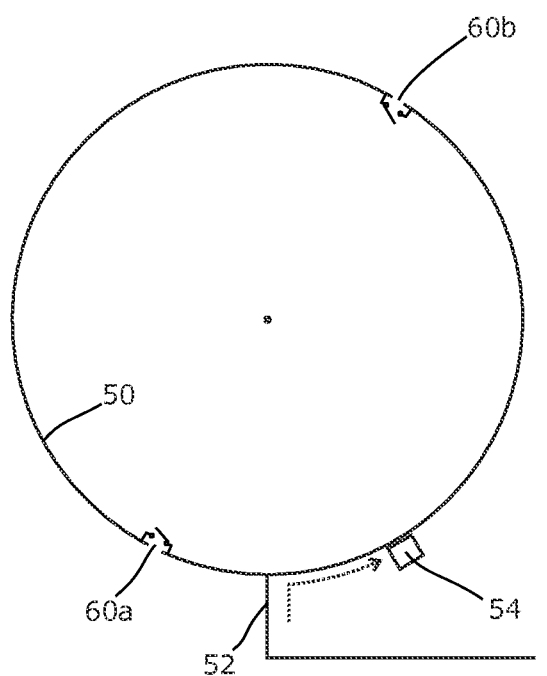

ial to the slip ring greater than the length of the at least one
RADIOTHERAPEUTIC APPARATUS This application is a continuation of Patent Cooperation Treaty Patent Application PCT/EP2011/006100, filed Dec. 6, 2011; which in turn claims priority from GB Patent Application 1105368.3, filed Mar. 30, 2011 and from GB Patent Application 1020805.6, filed Dec. 8, 2010; all of which are incorporated herein by reference.

FIELD OF THE INVENTION

The present invention relates to apparatus for the delivery of radiotherapy.

BACKGROUND ART

Radiotherapeutic apparatus is well-known, and consists of a source of radiation which emits a beam of radiation that is directed toward a patient in order to destroy or otherwise harm cancerous cells within the patient. Usually, the beam is collimated in order to limit its spatial extent to a desired region within the patient, such as the tumour or a sub-section of the tumour. The source can be a linear accelerator for high-energy (MV) x-radiation, or an isotopic source such as Co-60.

The source is often rotated around the patient in order to irradiate the desired region from a number of different directions, thereby reducing the dose applied to healthy tissue lying around the desired region. The shape of the desired region can be changed dynamically as the source rotates, in order to build up a complex dose distribution for tumours with more challenging shapes and/or which are located near to sensitive areas.

As the dose distribution becomes more closely tied to the exact shape of the tumour, and as the accuracy of the dose delivery improves, it has become necessary to know the current position of the patient, their internal organs, and the tumour with greater accuracy. As a result, low-energy x-ray sources are often provided on the apparatus in addition to the high-energy therapeutic source, to allow for x-ray or CT imaging of the patient before or during treatment. Portal imagers are often provided, which detect the therapeutic beam after attenuation by the patient. Both provide a degree of information as to the patient, but are subject to the inherent limitations of x-ray imaging, in particular the poor contrast obtained in areas of soft tissue. Generally, x-ray imaging is able to provide good contrast between areas of bone, soft tissue, and air, which allows for the detection of the gross patient position but has difficulty in detecting internal movements of the patient and the sub-structure within the soft tissue.

Efforts have therefore been directed towards combining a radiotherapy source with an MRI imager. MRI provides contrast within soft tissue, and is therefore suitable. However, there are significant practical problems in combining these two very different technologies.

SUMMARY OF THE INVENTION

In a magnetic resonance imaging (MRI) scanner, a static magnetic field is generated by way of a main magnet, usually provided with electrically superconducting main magnet coils, and is used to align nuclear spins as part as the procedure for producing images within the body of a patient to be examined. During an MRI scan, radiofrequency (RF) pulses are generated by RF transmitter antennae (coils) to cause perturbations to the local magnetic field, notably to tip the aligned nuclear spins. Magnetic resonance signals are acquired by RF receiver coils. These magnetic resonance signals are used to reconstruct the magnetic resonance images. Moreover, gradient coils are provided to generate temporary gradient magnetic field pulses for spatial encoding of the magnetic resonance signals.

One practical problem in combining an MRI scanner and a radiotherapy source is the delivery of power to the source. Linear accelerators have significant power demands, typically in the region of 10-14 kW. Delivered via a standard 415V three-phase supply, this therefore involves current flows of up to 30 A. Isotopic sources also need power in order to operate collimators and the like, although their current demands will usually be somewhat lower. Given that the source needs to rotate around the patient, this power will usually be delivered by way of a slip ring arrangement. This involves conducting the current via a conductor that follows a circumferential path around (or within) the MRI coils; notably, this is aligned with the main and gradient magnetic fields as well as with the magnetic fields emitted by the RF transmitter antennae and the magnetic fields associated with the magnetic resonance signals. This has the ability to create stray magnetic fields that interfere with the MRI field(s) and degrade the image quality.

We therefore provide a radiotherapeutic apparatus comprising a patient support, magnetic coils disposed around the patient support for creating a magnetic field therewithin, a radiation source producing a beam of radiation directed toward the patient support and mounted on a rotatable support thereby to rotate the radiation source around the patient support, a slip ring for conveying electrical power to the radiation source and located around the patient support, including at least one electrical interruption therein. This creates a slip ring in which there is no continuous circumferential path, i.e. one in which the current is therefore forced to take a route via one side or the other.

The at least one electrical interruption can be formed by a non-conductive section such as a break in the ring. Suitable forms of break include an air gap, a section of non-conductive material inserted into the ring, a switch, or a switched section. or a break filled with an electrical insulator.

The radiotherapeutic apparatus preferably further comprises an imaging means, notably in the form of an RF receiver system with one or several RF receiver antennae for detecting the magnetic resonance signals and deriving an image therefrom. Often the RF receiver antenna is formed by an RF receiver coil. Notably, the magnetic resonance image is reconstructed from the magnetic resonance signals by way of a fast Fourier transform.

A control means can be provided for the imaging means, adapted to detect when the rotatable support is in a position corresponding to the at least one non-conductive section and suppress the imaging means. This eliminates a transient disturbance to the imaging means at the moment when the current in the ring changes its route.

The radiation source can be a linear accelerator.

The rotatable support will usually include at least one brush contact, arranged to contact the slip ring. The or each brush contact preferably has a length in a direction tangential to the slip ring greater than the length of the at least one non-conducting section therein, to allow for continuous delivery of power. Alternatively, the at least one brush contact can have a length in a direction tangential to the slip ring smaller than the length of the at least one non-conducting section therein, but this will involve a temporary loss of power to the accelerator.

In another arrangement, the slip ring can be arranged to rotate with the rotatable support, and two or more rotationally stationary brush contacts can be provided, arranged to contact the slip ring. These can be arranged a greater distance apart than the length of said at least one non-conductive section.

The slip ring can also comprise a plurality of non-conductive sections, thus defining a plurality of electrically separate slip ring segments. Each slip ring segment can be separately and selectively coupled to a power source.

In another aspect, the present invention provides a treatment planning apparatus, arranged to produce a treatment plan suitable for a radiotherapeutic apparatus comprising a patient support, magnetic coils disposed around the patient support for creating a magnetic field therewithin, a radiation source producing a beam of radiation directed toward the patient support and mounted on a rotatable support thereby to rotate the radiation source around the patient support, and a slip ring for conveying electrical power to the radiation source and located around the patient support, including at least one non-conductive section therein, the treatment planning apparatus comprising an input for receiving clinical parameters, including at least imaging data of a patient in which areas for treatment have been identified, and geometric constraints including at least the location of the at least one non-conductive section in the slip ring, processing circuitry, for generating a treatment plan based at least on said clinical parameters and said geometric constraints, in which the operation of said radiation source is suppressed when the position of said rotatable source corresponds to the location of the at least one non-conductive section; and an output for outputting said treatment plan.

In a still further aspect, the present invention further provides a method of generating a treatment plan suitable for a radiotherapeutic apparatus comprising a patient support, magnetic coils disposed around the patient support for creating a magnetic field therewithin, a radiation source producing a beam of radiation directed toward the patient support and mounted on a rotatable support thereby to rotate the radiation source around the patient support, and a slip ring for conveying electrical power to the radiation source and located around the patient support, including at least one non-conductive section therein, the method comprising receiving clinical parameters, including at least imaging data of a patient in which areas for treatment have been identified, and geometric constraints including at least the location of the at least one non-conductive section in the slip ring, generating a treatment plan based at least on said clinical parameters and said geometric constraints, in which the operation of said radiation source is suppressed when the position of said rotatable source corresponds to the location of the at least one non-conductive section; and outputting said treatment plan.

In a further embodiment of the invention the slip ring comprises at least two switching means for selectively separating the slip ring into at least two electrically separate arc segments. A control means can be provided, to control the plurality of switching means based on the position of the rotatable support in relation to the slip ring. This should be done so that the radiation source is continuously powered regardless of the position of the rotatable support in relation to the slip ring, but that at least one of the switching means is open at any one time. The rotatable support can comprise at least one brush contact arranged to contact the slip ring.

BRIEF DESCRIPTION OF THE DRAWINGS

An embodiment of the present invention will now be described by way of example, with reference to the accompanying figures in which;

FIGS. 8 to 11 show sequential steps in the operation of the slip ring of FIG. 7.

DETAILED DESCRIPTION OF THE EMBODIMENTS

Figure 1:
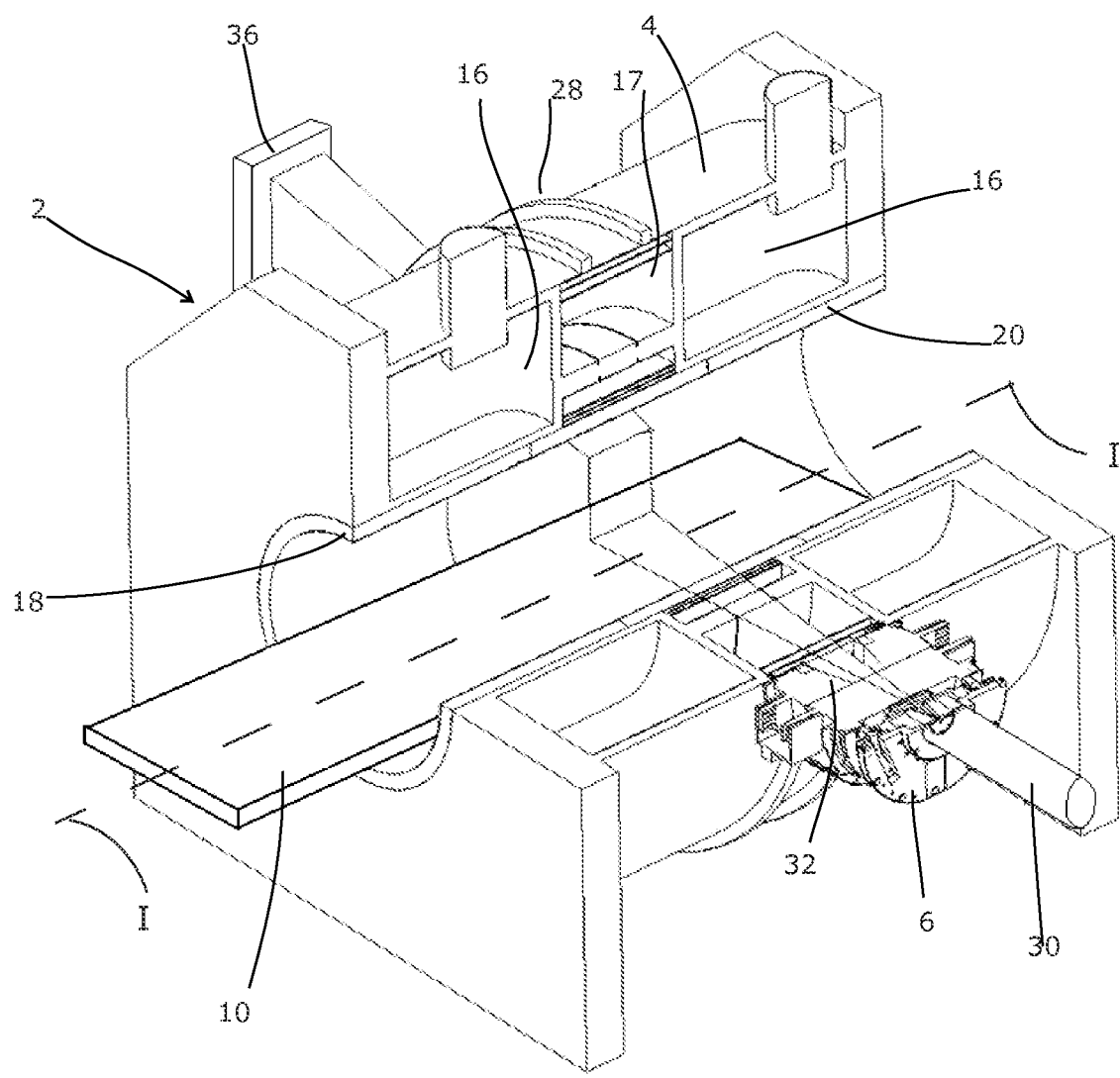
FIG. 1 shows a combined MRI and linear accelerator apparatus.

FIG. 1 shows a system 2 according to embodiments of the present invention, comprising a radiotherapy apparatus 6 and a magnetic resonance imaging (MRI) apparatus 4.

The system includes a couch 10, for supporting a patient in the apparatus. The couch 10 is movable along a horizontal, translation axis (labelled "I"), such that a patient resting on the couch is moved into the radiotherapy and MRI apparatus. In one embodiment, the couch 10 is rotatable around a central vertical axis of rotation, transverse to the translation axis, although this is not illustrated. The couch 10 may form a cantilever section that projects away from a support structure (not illustrated). In one embodiment, the couch 10 is moved along the translation axis relative to the support structure in order to form the cantilever section, i.e. the cantilever section increases in length as the couch is moved and the lift remains stationary. In another embodiment, both the support structure and the couch 10 move along the translation axis, such that the cantilever section remains substantially constant in length, as described in the U.S. patent application Ser. No. 11/827,320 filed on 11 Jul. 2007.

As mentioned above, the system 2 also comprises an MRI apparatus 4, for producing near real-time imaging of a patient positioned on the couch 10. The MRI apparatus includes a primary magnet 16 which acts to generate the so-called "primary" magnetic field for magnetic resonance imaging. That is, the magnetic field lines generated by operation of the magnet 16 run substantially parallel to the central translation axis I. The primary magnet 16 consists of one or more coils with an axis that runs parallel to the translation axis I. The one or more coils may be a single coil or a plurality of coaxial coils of different diameter. In one embodiment (illustrated), the one or more coils in the primary magnet 16 are spaced such that a central window 17 of the magnet 16 is free of coils. In other embodiments, the coils in the magnet 16 may simply be thin enough that they are substantially transparent to radiation of the wavelength generated by the radiotherapy apparatus. The magnet 16 may further comprise one or more active shielding coils, which generates a magnetic field outside the magnet 16 of approximately equal magnitude and opposite polarity to the external primary magnetic field. The more sensitive parts of the system 2, such as the accelerator, are positioned in this region outside the magnet 16 where the magnetic field is cancelled, at least to a first order.

The MRI apparatus 4 further comprises two gradient coils 18, 20, which generate the so-called "gradient" magnetic field that is superposed on the primary magnetic field. These coils 18, 20 generate a gradient in the resultant magnetic field that allows spatial encoding of the protons so that their position can be determined, for example the gradient coils 18, can be controlled such that the imaging data obtained has a particular orientation. The gradient coils 18, 20 are positioned around a common central axis with the primary magnet 16, and are displaced from one another along that central axis. This displacement creates a gap, or window, between the two coils 18, 20. In an embodiment where the primary magnet 16 also comprises a central window between coils, the two windows are aligned with one another.

An RF system causes the protons to alter their alignment relative to the magnetic field. When the RF electromagnetic field is turned off the protons return to the original magnetization alignment. These alignment changes create a signal which can be detected by scanning. The RF system may include a single coil that both transmits the radio signals and receives the reflected signals, dedicated transmitting and receiving coils, or multi-element phased array coils, for example. Control circuitry controls the operation of the various coils 16, 18, 20 and the RF system, and signal-processing circuitry receives the output of the RF system, generating therefrom images of the patient supported by the couch 10.

As mentioned above, the system 2 further comprises a radiotherapy apparatus 6 which delivers doses of radiation to a patient supported by the couch 10. The majority of the radiotherapy apparatus 6, including at least a source of radiation 30 (e.g. an x-ray source and a linear accelerator) and a multi-leaf collimator (MLC) 32, is mounted on a chassis 28. The chassis 28 is continuously rotatable around the couch 10 when it is inserted into the treatment area, powered by one or more chassis motors. In the illustrated embodiment, a radiation detector 36 is also mounted on the chassis 28 opposite the radiation source 30 and with the rotational axis of the chassis positioned between them. The radiotherapy apparatus 6 further comprises control circuitry, which may be integrated within the system 2 shown in FIG. 1 or remote from it, and controls the radiation source 30, the MLC 32 and the chassis motor.

In other embodiments, the radiotherapy apparatus 6 may comprise more than one source and more than one respective multi-leaf collimator. Notably, each source may have its own MLC associated with it to shape the beam of that source.

The radiation source 30 is positioned to emit a beam of radiation through the window defined by the two gradient coils 18, 20, and also through the window defined in the primary magnet 16. The radiation beam may be a cone beam or a fan beam, for example.

In operation, a patient is placed on the couch 10 and the couch is inserted into the treatment area defined by the magnetic coils 16, 18 and the chassis 28. The control circuitry 38 controls the radiation source 30, the MLC 32 and the chassis motor to deliver radiation to the patient through the window between the coils 16, 18. The chassis motor is controlled such that the chassis 28 rotates about the patient, meaning the radiation can be delivered from different directions. The MLC 32 has a plurality of elongate leaves oriented orthogonal to the beam axis; an example is illustrated and described in the European patent application EP-A-0,314,214, the content of which is hereby incorporated by reference and to which the reader is directed in order to obtain a full understanding of the described embodiment. The leaves of the MLC 32 are controlled to take different positions blocking or allowing through some or all of the radiation beam, thereby altering the shape of the beam as it will reach the patient. Simultaneously with rotation of the chassis 28 about the patient, the couch 10 may be moved along a translation axis into or out of the treatment area (i.e. parallel to the axis of rotation of the chassis). With this simultaneous motion a helical radiation delivery pattern is achieved, known to produce high quality dose distributions.

The MRI apparatus 4, and specifically the signal-processing circuitry, delivers real-time (or in practice near real-time) imaging data of the patient to the control circuitry. This information allows the control circuitry to adapt the operation of the MLC 32, for example, such that the radiation delivered to the patient accurately tracks the motion of the target region, for example due to breathing.

Clearly, the radiotherapy apparatus 6 will have a significant power consumption, mainly due to the need to power the linear accelerator 30, but also the collimator 32 and the like. This needs to be transmitted to the rotating chassis 28, which would normally be achieved via a slip ring. These consist of a number of longitudinally spaced conductive circular rings to which power is fed from a fixed connection and from which power is drawn via a brush contact that can slide (or slip) circumferentially around the ring. The brush contacts can be mounted on the chassis 28 and thus power is transmitted from a fixed supply to the rotating chassis. This allows the chassis to rotate continuously around the couch 10. The alternative, a flexible conduit linking the chassis 28 or the radiotherapy apparatus 6 to a fixed point, requires that there be limitations on the range of angular movement of the radiotherapy apparatus 6.

A slip ring has the problem that the current drawn (even from a 415V supply) could have a significant disruptive effect on the magnetic fields produced by the primary coil 16 and the gradient coils 18, 20, if it is not properly controlled. The slip rings, by their nature, extend around the couch 10 and thus have a coil form and are capable of creating a magnetic field. Their coil strength is not large, but the currents flowing in them may be substantial and thus the magnetic field created by those currents may be significant relative to the magnetic fields being created by the primary coil 16 and the gradient coils 18, 20. This could therefore adversely affect the quality of the images produced by the MRI system.

Figure 2:
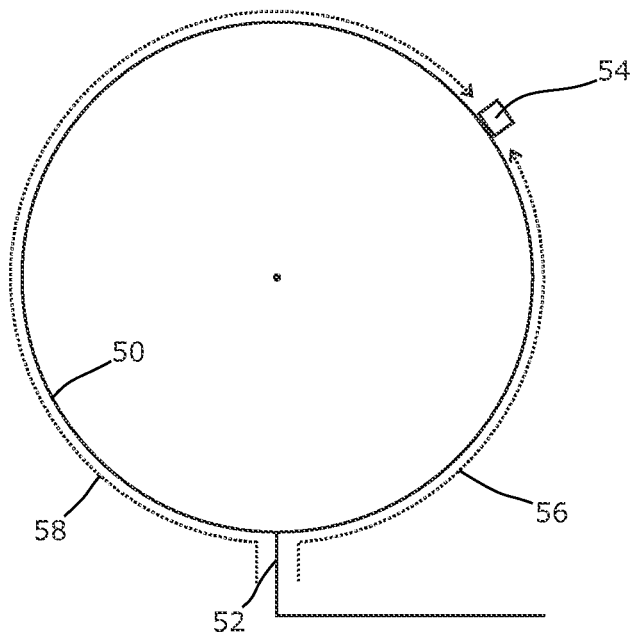
FIG. 2 shows the effect of a conventional slip ring.
Figure 3:
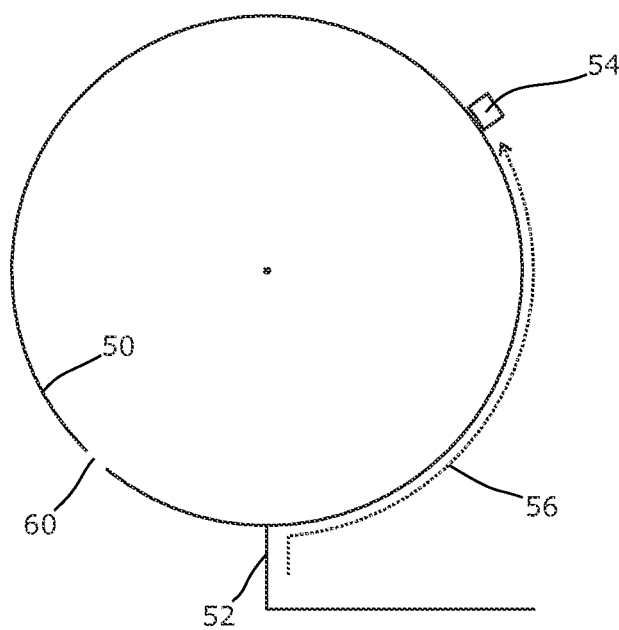
FIG. 3 shows a slip ring according to the present invention.

Referring to FIG. 2, if we assume that current is supplied to a slip ring conductor 50 at its base 52 and is extracted by the movable brush contact 54 at a different point on the ring 50, then a current flow has a choice of two alternative directions 56, 58 around the ring 50. In theory, the current will primarily take the path of least resistance, i.e. the shorter of the two paths 56, splitting between the two rings proportionately to their length (and hence their resistance) in accordance with Ohm's law. However, in practice the manufacturing tolerances of the slip rings, combined with the wear created by movement of the brush 54 along their surface, will mean that the ring conductor 50 is not perfectly uniform around its length and therefore the division of the current is not wholly predictable.

It must also be remembered that the ring conductor 50 is one of three such conductors, one for each of the three phases of the AC supply used by the radiotherapy apparatus. Each conductor will have a different distribution of non-uniformities and thus the three currents, whilst adding up to zero, may involve different local currents divided in different ways between the six possible paths (two paths for each of the three conductors).

As a result, it is impossible to predict exactly what pattern of currents might exist at any one time, and entirely possible that at some times there may be a significant net current, provided collectively by the three conductors, in the circular path around the couch 10. This will then create a significant magnetic field longitudinally within the apparatus, which will disturb the imaging process.

According to the present invention, therefore, we provide a break 60 in the slip ring conductor 50. The position of the break is not especially important, so it can be located anywhere that is convenient from the perspective of engineering and therapeutic considerations. Equally, the precise nature of the break is not important, so long as electrical conduction across the break can be prevented or made substantially impossible. Thus, the break can be an air gap, a section of non-conductive material inserted into the ring, a switch, or a switched section. It means that the current has no choice as to route but must pass to the brush contact 54 via one route 56.

The question then arises as to how to cope when the radiotherapy apparatus transits past the location of the break 60 as part of its rotational movement. This can be dealt with in several ways.

First, the brush 54 could be made (circumferentially) longer than the break 60. This will enable the leading edge of the brush 54 to make contact with the opposite side of the break before its trailing edge loses contact. A continuous supply of current will then be supplied to the radiotherapy apparatus, enabling it to operate continuously as it rotates around the patient. There may well be a brief transient magnetic field as the brush 54 bridges the break 60 (and therefore re-creates a continuous ring), so the imaging system should be de-activated or otherwise prevented from acquiring (or using) images or data from this moment in time.

Figure 4:
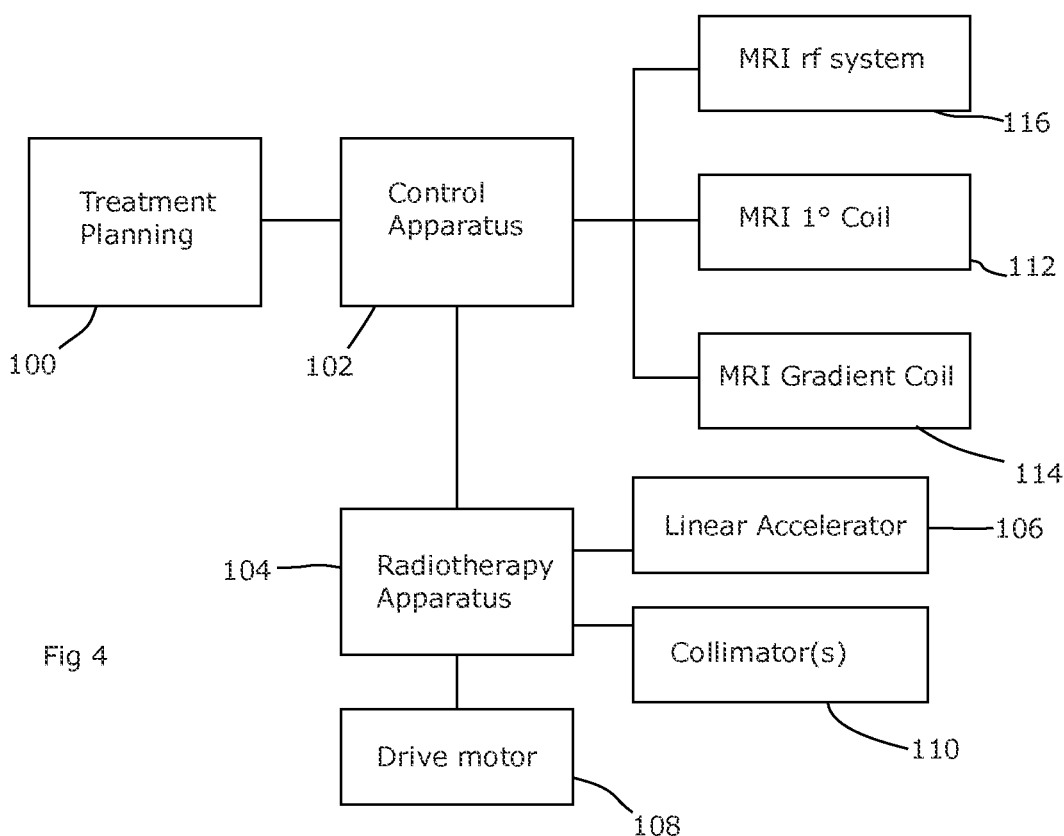
FIG. 4 shows a schematic arrangement of the elements making up a radiotherapy apparatus according to the present invention.

Second, the brush 54 could be made (circumferentially) shorter than the break 60, resulting in a brief loss of power to the radiotherapy apparatus during that moment. Generally, the rotational drive to the chassis 28 carrying the radiotherapy apparatus is provided by a drive motor that is fixed and can therefore have its own power supply, so this interruption will only disable the linear accelerator and the radiotherapy apparatus will be able to continue rotating past the break 60. Thus, it is only necessary to program the treatment planning system with the additional constraint that no therapeutic beam can be produced at (or, in practice, within a certain margin around) angles corresponding to the break 60.

Where a brief interruption to power delivery is envisaged, or otherwise, it may be useful to provide a power buffer in the rotating chassis 28, such as a battery or capacitor (for DC systems) or an inductor (for AC systems). FIG. 4 shows the schematic arrangement of the system. A treatment planning system 100 is loaded with the desired dose distribution and the various apparatus constraints (which can include non-treatable angles, as noted above) and produces a treatment plan consisting of beam shapes and doses to be delivered from specific rotational directions. This is passed to a control apparatus 102 which sends instructions to the radiotherapy apparatus 104 to rotate the linear accelerator 106 to the desired position using the drive motor 108 and set the collimator(s) 110 as required. The control apparatus 102 also instructs the MRI primary coils 112, gradient coils 114 and rf system 116 as required in order to obtain images of the patient prior to, during, and/or after treatment The control apparatus 102 may also, as noted above, de-activate the MRI system or otherwise prevent it from acquiring (or using) images or data while the radiotherapy apparatus is crossing the break 60.

Figure 5:
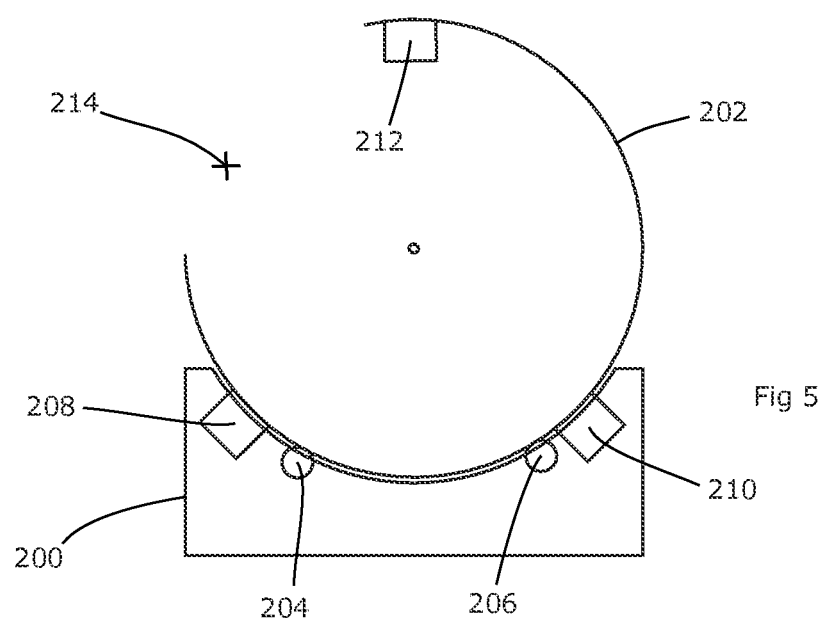
FIGS. 5 and 6 show an alternative design of slip ring according to the present invention.
Figure 6:
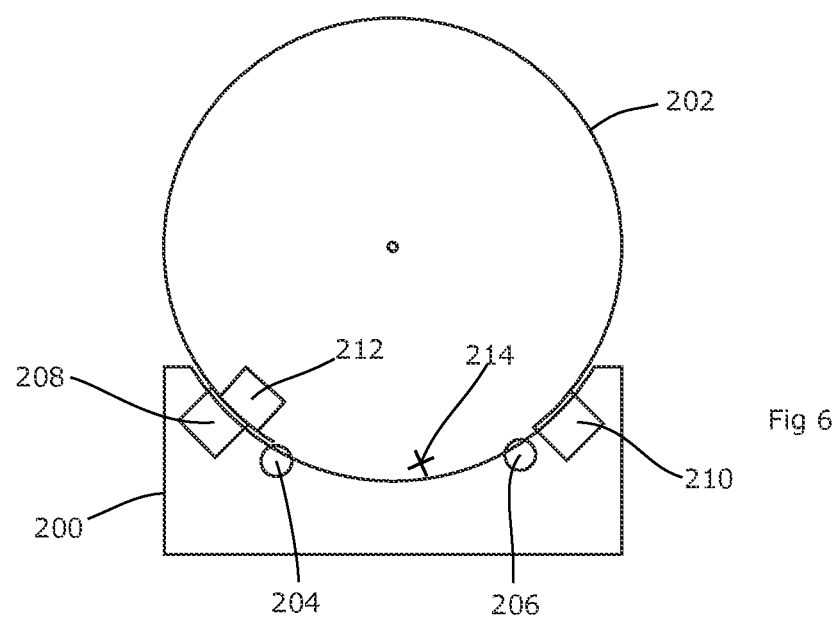

FIGS. 5 and 6 show an alternative implementation of the break in the slip ring, allowing continuous delivery of power and continuous imaging. FIG. 5 shows a schematic vertical section through the apparatus, viewed along the longitudinal axis I of FIG. 1. A base unit 200 is fixed to a floor or other suitable substrate, and supports a rotatable chassis (omitted for clarity) on which is mounted a part-circular slip ring 202. The chassis is driven and partially supported by drive rollers 204, 206.

Thus, the slip ring 202 is, in this embodiment, carried by the rotating chassis and rotates with the chassis. Power is delivered to the slip ring 202 by two brush contacts 208, 210 that are fixedly mounted in the base 200. Power is delivered to the radiotherapy apparatus by a contact 212 fixedly mounted on an inner radial face of the slip ring 202.

Thus, contrary to the above embodiments, the slip ring 202 rotates with the chassis, and the contacts on the base 200 slide over the ring 202 as the chassis is rotated by the drive rollers 204, 206.

The slip ring 202 is part-circular in that it has a break 214 which occupies a substantial angular section of the ring, in this case about 90°. This is filled with a non-conducting insert (not shown, for clarity) in order to avoid damage and/or disruption to the brush contacts 208, 210. The angular extent of the break 214 is somewhat less than the angular separation of the two brushes 208, 210, which is in this case about 100°.

In the position shown in FIG. 5, the break 214 is away from the brushes, leaving only one possible electrical path to the radiotherapy apparatus, which is via either brush 208, 210, along the slip ring 202, and out via the contact 212. No circular path exists, and therefore no unwanted magnetic fields will be created. In this state, the embodiment acts in the same way as the previous embodiments, save that the slip ring is rotating instead of being stationary.

As the chassis, radiotherapy apparatus, and slip ring rotate, eventually the break will reach one of the brush contacts 208, 210. At this point, that brush contact will become redundant, but power can still be supplied via the other brush contact, passing around the slip ring 202 to the contact 212. There is still no circular path.

Eventually, after further rotation, the state shown in FIG. 6 will be reached where the break 214 is about to reach (but has not quite reached) the other brush contact. At this point, the fact that the angular extent of the break 214 is less than the angular separation of the brush contacts 208, 210 will mean that the first brush contact will have regained contact with the slip ring 202. Therefore, at least one brush contact will always be able to supply power to the rotating slip ring 202. It only remains to ensure that the cables or conductors supplying power to the brush contacts 208, 210 do not themselves serve to complete the circular path, such as by providing two separate conductors which approach the brush contacts 208, 210 in a longitudinal direction or a radially inward direction.

According to the present invention, therefore, we provide at least two switched breaks 60a and 60b in the slip ring conductor 50, dividing it into two sections. The positions of the breaks are not especially important, so it is convenient to divide the ring into equal sections.

Figure 7:
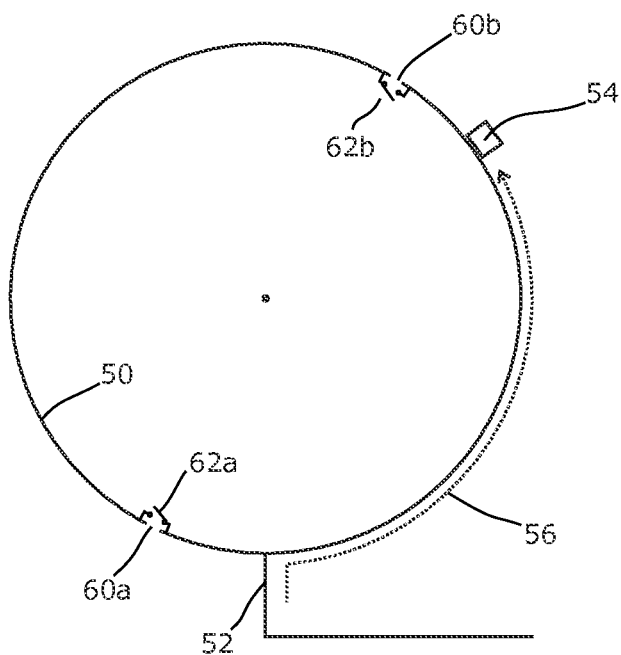
FIG. 7 shows a slip ring according to the present invention in which switches are employed.

Equally, the precise nature of the break is not important, so long as electrical conduction across the break can be controlled. Thus, the break can be an air gap, or a section of non-conductive material inserted into the ring, or some other interruption to the conductivity of the ring, together with a switch 62a, 62b that bridges the interruption and allows current to bypass the break when desired. As illustrated in FIG. 7, the switches can be controlled so as to limit the available current paths to only a single path 56.

FIGS. 8 to 11 show sequential steps in the operation of the apparatus. In the version illustrated, the conductive rings 50 are stationary and all have identical patterns of switched breaks, a lower switched break 60a at seven o'clock and an upper switched break 60b at one o'clock (when viewed along their axis). A set of brushes 54 are provided, one for each of the three rings that supply each of the three phases of an AC supply. The brushes are all in substantially the same circumferential position. Thus, the single ring & brush shown in FIGS. 4 to 7 does in fact show the situation of all three rings and brushes. Some or all of these factors could be relaxed or varied in a preferred implementation in order to create a more complex system, but for the purpose of explanation the illustrated arrangement will suffice.

Figure 8:
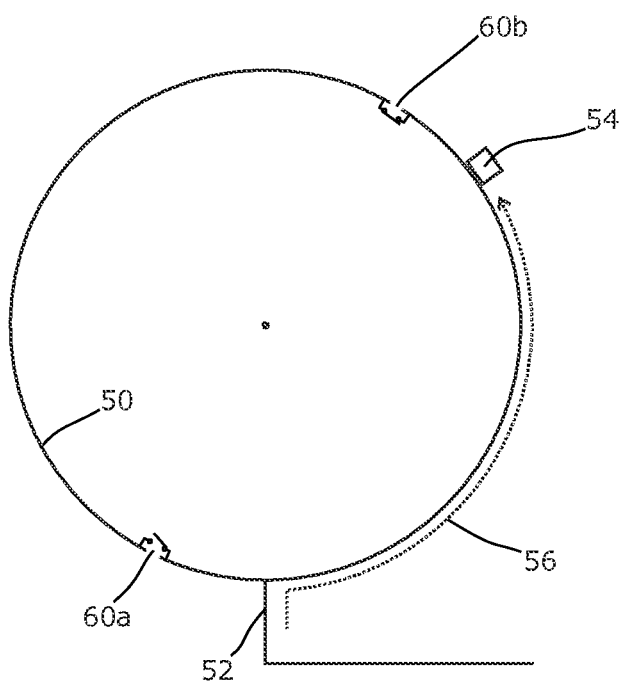

Thus, in FIG. 8 the brushes 54 are at about 2 o'clock and are moving in an anticlockwise direction towards the upper switched break 60b. This switched break 60b is therefore closed in anticipation of the brush 54 passing by. The lower switched break 60a is open (i.e. non-conductive) thereby ensuring that there are no continuous paths around the apparatus. This means that there is only one possible path 56 from the base 52 at which current is supplied to the brush 54.

Figure 9:
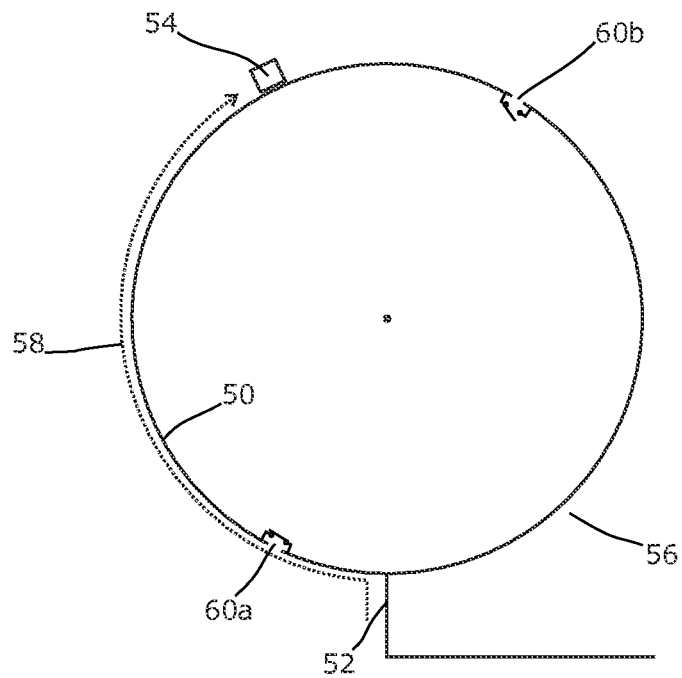

After the brush 54 has passed the upper switched break 60b, as shown in FIG. 9, this can be opened and the lower switched break 60a closed. This will create a new conduction path 58 via the lower switched break 60a and break the previous conductive path, thereby ensuring that there remain no continuous paths around the apparatus. The changing of the two switches can be done substantially simultaneously, if the switching and control mechanisms are capable of doing so reliably. Alternatively, the upper switch 62b can be opened marginally before the lower switch 62a is closed, thereby creating a brief hiatus in power supply but ensuring that there is never a continuous path around the apparatus. In a further alternative, the upper switch 62b can be opened marginally after the lower switch 62a is closed, thereby maintaining continuity of power at the expense of a brief moment during which a continuous path exists. In this latter case, the possible fleeting disruption to the imaging system can be accepted, or imaging can be momentarily suspended, or the exact moment of switching can be timed so as to co-incide with an interruption to imaging. The use of multiple switches does of course mean that the change-over can be at any time while the brush 54 is in the relevant section between the switches, thus allowing a degree of freedom in timing the change-over.

Where a brief interruption to power delivery is envisaged, or otherwise, it may be useful to provide a power buffer in the rotating chassis 28, such as a battery or capacitor (for DC systems) or an inductor (for AC systems).

Figure 10:
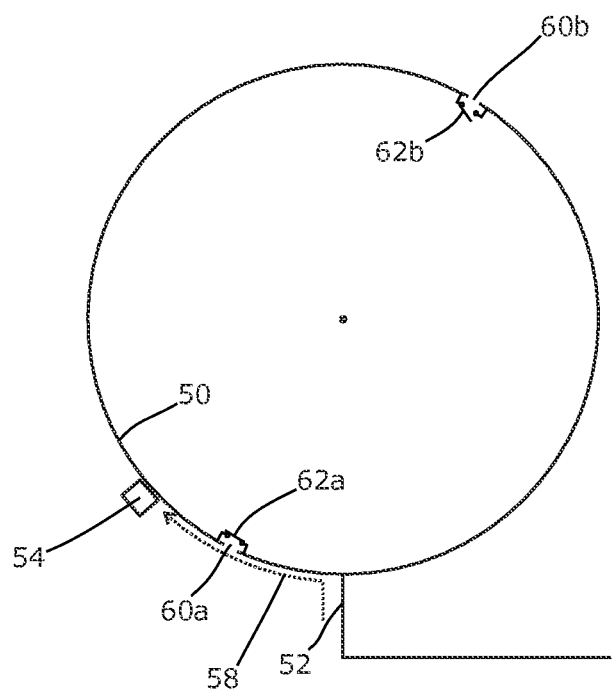

FIG. 10 shows the situation after further anti-clockwise rotation of the brush 54, to a position shortly before the lower switched break 60a. This is still in a closed state, allowing a short conduction path 58 from the base 52 via the lower switch 62a. The alternative conduction path is prevented by the upper switch 62b being open. FIG. 6 illustrates the approximate point by which the changeover in conduction paths discussed above needs to have been made.

FIG. 11 shows the apparatus after the brush 54 has passed the lower switched break 60a. The lower switch 62a can then be opened, and the upper switch 62b closed. Note that the upper switch can be closed after the lower switch 62a is opened, as the brush 54 is in the same section of ring 50 as the current supply from the base 52. Thus, a supply of power is assured regardless of the state of the various switches, and it is acceptable for both (or all) the switches to be open. Accordingly, a "break before make" arrangement is preferable as it does not raise any complications.

As the brush 54 continues to rotate anticlockwise, the process then repeats. Of course, for clockwise rotation the process should be reversed. Some treatment plans call for variability in the rotational motion of the treatment head, rotating in a first direction for a first period, then reversing and moving in the opposite direction, followed (potentially) by further reversals. In such a case, the switches can be controlled appropriately according to the above principles, depending on the instantaneous direction of rotation. It may be advantageous for there to be a flow of information as to the future rotation to the control means governing the switches, or for the switching to be decided in advance during (or following) the treatment planning stage once the desired rotational trajectory has been set.

The control apparatus 102 may also, as noted above, de-activate the MRI system or otherwise prevent it from acquiring (or using) images or data while the switches 62a, 62b are being changed simultaneously or near-simultaneously.

Thus, embodiments of the invention are able to provide a satisfactory power supply to a rotating radiotherapy apparatus without at any time allowing current to be conducted in a circular path around the longitudinal axis.

Thus, embodiments of the invention are able to provide a satisfactory power supply to a rotating radiotherapy apparatus without at any time allowing current to be conducted in a circular path around the longitudinal axis.

It will of course be understood that many variations may be made to the above-described embodiment without departing from the scope of the present invention.

The invention claimed is:

1. A radiotherapeutic system comprising:
a patient support;
a magnetic resonance examination system with magnetic coils disposed around the patient support for creating a magnetic field therewithin and configured for detecting magnetic resonance signals and deriving images therefrom;
a radiotherapeutic radiation source producing a beam of radiotherapeutic radiation directed toward the patient support and mounted on a rotatable support thereby to rotate the radiation source around the patient support, and
a slip ring located around the patient support and configured to convey electrical power provided from a base to the radiation source, wherein the slip ring includes at least one electrical interruption formed by at least one non-conductive section in the slip ring, and the rotatable support includes at least one brush contact arranged to contact the slip ring, wherein the at least one electrical interruption provides only one path of current along the slip ring from the base to which current is being supplied to the brush so as to prevent a stray magnetic field generated by rotation of the rotatable support around the slip ring from interfering with images produced by the magnetic resonance examination system;
a control apparatus coupled to the radiotherapeutic radiation source, wherein the control apparatus is configured to control the radiotherapeutic radiation source and to perform at least one of:
 i. de-activating the magnetic resonance examination system while the at least one brush contact is crossing the at least one non-conductive section, and ii. preventing the magnetic resonance examination system from acquiring or using imaging data while the at least one brush contact is crossing the at least one non-conductive section.

2. The radiotherapeutic system according to claim 1, wherein the at least one non-conductive section is an air gap.

3. The radiotherapeutic system according to claim 1, wherein the at least one non-conductive section is a break filled with an electrical insulator.

4. The radiotherapeutic system according to claim 1, wherein the at least one brush contact has a length in a direction tangential to the slip ring greater than the length of the at least one non-conducting section therein.

5. The radiotherapeutic system according to claim 1, wherein the at least one brush contact has a length in a direction tangential to the slip ring smaller than the length of the at least one non-conducting section therein.

6. The radiotherapeutic system according to claim 1, wherein the radiation source is a linear accelerator.

7. The radiotherapeutic system according to claim 1, wherein the slip ring is arranged to rotate with the rotatable support, and further comprising two or more rotationally stationary brush contacts, arranged to contact the slip ring.

8. The radiotherapeutic system according to claim 7, wherein the two or more rotationally stationary brush contacts are arranged a greater distance apart than the length of said at least one non-conductive section.

9. The radiotherapeutic system according to claim 1, wherein the slip ring comprises a plurality of electrical interruptions defining a plurality of electrically separate slip ring segments.

10. The radiotherapeutic system according to claim 9, wherein each slip ring segment is separately and selectively coupled to a power source.

11. The radiotherapeutic system according to claim 1, wherein the slip ring comprises at least two switches, forming the electrical interruption for selectively separating the slip ring into at least two electrically separate arc segments.

12. The radiotherapeutic system according to claim 11, wherein the magnetic resonance examination system is further configured to control the at least two switches according to a position of the rotatable support in relation to the slip ring.

13. The radiotherapeutic system according to claim 12 wherein the magnetic resonance examination system is configured to control the at least two switches such that the radiation source is continuously powered regardless of the position of the rotatable support in relation to the slip ring.

14. A treatment planning apparatus configured to produce a treatment plan configured for a radiotherapeutic system, wherein the treatment planning apparatus comprises the radiotherapeutic system with a patient support, a magnetic resonance examination system with magnetic coils disposed around the patient support for creating a magnetic field therewithin, a radiotherapeutic radiation source producing a beam of radiotherapeutic radiation directed toward the patient support and mounted on a rotatable support thereby to rotate the radiation source around the patient support, and a slip ring located around the patient support and configured to convey electrical power provided from a base to the radiation source, wherein the slip ring includes at least one electrical interruption formed by at least one non-conductive section in the slip ring, and the rotatable support includes at least one brush contact, arranged to contact the slip ring, wherein the at least one electrical interruption provides only one path of current along the slip ring from the base to which current is being supplied to the brush so as to prevent a stray magnetic field generated by rotation of the rotatable support around the slip ring from interfering with images produced by the magnetic resonance examination system; a processing circuitry for receiving clinical parameters including at least imaging data of a patient in which areas for treatment have been identified, and geometric constraints including at least the location of the at least one electrical interruption in the slip ring;

wherein the processing circuitry further configured to generate a treatment plan based at least on said clinical parameters and said geometric constraints, in which the operation of said radiation source is suppressed when the position of said rotatable source corresponds to the location of the at least one electrical interruption; and wherein the processing circuitry further configured to output said treatment plan.

15. A method of generating a treatment plan configured for a radiotherapeutic system comprising a patient support, a magnetic resonance examination system with magnetic coils disposed around the patient support for creating a magnetic field therewithin, a radiotherapeutic radiation source configured to produce a beam of radiotherapeutic radiation directed toward the patient support and mounted on a rotatable support thereby to rotate the radiation source around the patient support, and a slip ring located around the patient support and configured to convey electrical power provided from a base to the radiation source, wherein the slip ring includes at least one electrical interruption formed by at least one non-conductive section in the slip ring, and the rotatable support includes at least one brush contact arranged to contact the slip ring, wherein the at least one electrical interruption provides only one path of current along the slip ring from the base to which current is being supplied to the brush so as to prevent a stray magnetic field generated by rotation of the rotatable support around the slip ring from interfering with images produced by the magnetic resonance examination system, the method comprising:

receiving clinical parameters, including at least imaging data of a patient in which areas for treatment have been identified, and geometric constraints including at least the location of the at least one electrical interruption in the slip ring;

generating a treatment plan based at least on said clinical parameters and said geometric constraints, in which the operation of said radiation source is suppressed when the position of said rotatable source corresponds to the location of the at least one electrical interruption; and outputting said treatment plan.

* * * * *